United States Patent
Muhl et al.

(10) Patent No.: US 7,719,289 B2
(45) Date of Patent: May 18, 2010

(54) MEASURING DEVICE FOR MEASURING THE STATE OF OILS OR FATS

(75) Inventors: Mike Muhl, Freiburg (DE); Juergen Hall, Friedenweiler (DE)

(73) Assignee: Testo AG, Lenzkirch (DE)

(*) Notice: Subject to any disclaimer, the term of this patent is extended or adjusted under 35 U.S.C. 154(b) by 454 days.

(21) Appl. No.: 11/547,762

(22) PCT Filed: Mar. 30, 2005

(86) PCT No.: PCT/EP2005/003324

§ 371 (c)(1),
(2), (4) Date: Jun. 8, 2007

(87) PCT Pub. No.: WO2005/098407

PCT Pub. Date: Oct. 20, 2005

(65) Prior Publication Data

US 2007/0277594 A1 Dec. 6, 2007

(30) Foreign Application Priority Data

Apr. 6, 2004 (DE) .................. 10 2004 016 958

(51) Int. Cl.
G01N 27/416 (2006.01)
G01N 27/02 (2006.01)
(52) U.S. Cl. .................. 324/658; 324/437; 324/445
(58) Field of Classification Search .................. 324/658, 324/661, 662, 698
See application file for complete search history.

(56) References Cited

U.S. PATENT DOCUMENTS

| | | | | |
|---|---|---|---|---|
| 5,017,340 A | * | 5/1991 | Pribat et al. ........... | 422/98 |
| 5,313,168 A | * | 5/1994 | Ogawa .................. | 324/663 |
| 5,331,845 A | * | 7/1994 | Bals et al. .............. | 73/61.43 |
| 5,435,170 A | * | 7/1995 | Voelker et al. ......... | 73/53.05 |
| 5,929,754 A | * | 7/1999 | Park et al. ............. | 340/439 |
| 2003/0155935 A1 | * | 8/2003 | Klun ..................... | 324/664 |
| 2004/0057220 A1 | | 3/2004 | Tamaki et al. | |

FOREIGN PATENT DOCUMENTS

| | | |
|---|---|---|
| DE | 42 18 883 A1 | 12/1993 |
| DE | 198 27 542 A1 | 12/1999 |
| DE | 198 29 415 A1 | 1/2000 |
| DE | 101 63 760 A1 | 7/2003 |
| EP | 1 046 908 A | 10/2000 |
| EP | 1 324 036 A | 7/2003 |

* cited by examiner

*Primary Examiner*—Timothy J Dole
*Assistant Examiner*—Farhana Hoque
(74) *Attorney, Agent, or Firm*—Muirhead and Saturnelli, LLC

(57) ABSTRACT

A measuring device is used to measure the state of oils of fats. Said measuring device comprises a housing, a hollow connecting element which is secured therein and a carrier which is applied to the opposite end of the connecting element, said carrier being used to receive a sensor which can be used to measure an electric property of the product which is to be measured. The sensor is in contact with an evaluation unit by means of at least one electric line which is arranged on a non-conductive carrier, which is arranged in the region of the housing and/or the end of the connecting element which is oriented towards the housing. The measuring device comprises a plurality of carriers which are arranged in a row and which are thermally insulated from each other.

20 Claims, 3 Drawing Sheets

MEASURING DEVICE FOR MEASURING THE STATE OF OILS OR FATS

TECHNICAL FIELD

The present application relates to a measuring device for measuring the state of oils or fats.

BACKGROUND OF THE INVENTION

Hot oils or fats are often used not only once, but utilized in deep fryers over a longer period for successively preparing different foods. The oil or fat is decomposed by oxidation at the hot operating temperatures between approximately 120° and 180° C. and undesirable chemical products such as free fatty acids and polymers are formed, which do not only impair the taste, but may also have adverse health effects.

In order not to replace frying oils or fats too early or too late, measuring devices are used for measuring the state of oils or fats, including tests for their electrical properties. Measuring the dielectric constant, which is a reliable measure of the degree of decomposition of the fat or oil, is particularly suitable.

EP 1 046 908 A2, for example, describes a measuring device for measuring the state of an oil or fat, which has a housing which contains the electronic analyzing units and a data display, as well as a tubular connecting element with a sensor situated at its tip which may be directly immersed into the hot oil or fat and is suitable for determining the dielectric constant. The sensor and the electronic analyzer circuit are electrically connected via a cable laid freely within the connecting element.

DE 101 63 760 A1 describes a refinement of the above-mentioned measuring device. In the measuring device presented therein, the electrical conductors between sensor and electronic analyzer circuit are formed by metallic conductors printed on a ceramic substrate. The tubular connecting element is shaped in such a way that it surrounds most of the substrate and narrows downward so that only the area of the substrate on which the sensor is situated is accessible from the outside. An insulating sealing adhesive is introduced and cured between substrate and connecting element, so that there is no electrical connection between the connecting element and the electric conductors. In addition, a temperature-stable seal is thus achieved, which prevents the oil from penetrating inside the connecting element. A temperature sensor may also be provided, whose measurement results may also be processed by the electronic analyzer circuit.

The disadvantage of this device is, however, that heat is transferred from the oil or fat to be measured to the electronic analyzer circuit and thus the service life of the components is reduced and/or the accuracy of the measurement results is impaired.

Accordingly, it is desirable to provide a measuring device that would significantly reduce the temperature load on the electronic analyzer circuit and thus increase the service life of the electronic components.

SUMMARY OF THE INVENTION

According to an embodiment of the system described herein, a measuring device includes a substrate configuration that improves heat characteristics of the device. Due to the fact that the measuring device has a plurality of substrates arranged in series, significant heat transfer from the oil or fat to be measured to the first electronic circuit component is prevented and thus a lower heat load is produced which results in less effort for the compensation.

The substrates are preferably connected at the points of separation via metallic connecting elements for electrical coupling, which ensures isolation in a particularly simple manner.

In the sensor area, the track conductors on the first substrate have a small cross-section; therefore, a minimum amount of heat is injected into the substrate.

Thereafter, the track conductors preferably have a flat design, making a relatively homogeneous temperature distribution over the entire width of the substrate possible.

The use of substrates having a plurality of layers is particularly preferred so that an even more effective heat distribution on the individual substrates is ensured.

On areas of the substrate layers not occupied by track conductors and not in direct contact with the oil or fat to be measured, a compound may be applied to portions of the surface, which, due to its high specific heat, prevents a rapid increase in the substrate's temperature and, due to its high thermal conductivity, provides uniform temperature distribution in the substrate at the same time.

Further details, features, and advantages of the present invention are derived from the description that follows and the appended drawing.

BRIEF DESCRIPTION OF THE DRAWINGS

Embodiments of the system are described with reference to the several figures of the drawings, in which.

DETAILED DESCRIPTION OF VARIOUS EMBODIMENTS

Referring now to the figures of the drawings, the figures comprise a part of this specification and illustrate exemplary embodiments of the described system. It is to be understood that in some instances various aspects of the system may be shown schematically or may be exaggerated or altered to facilitate an understanding of the system.

Figure 1:
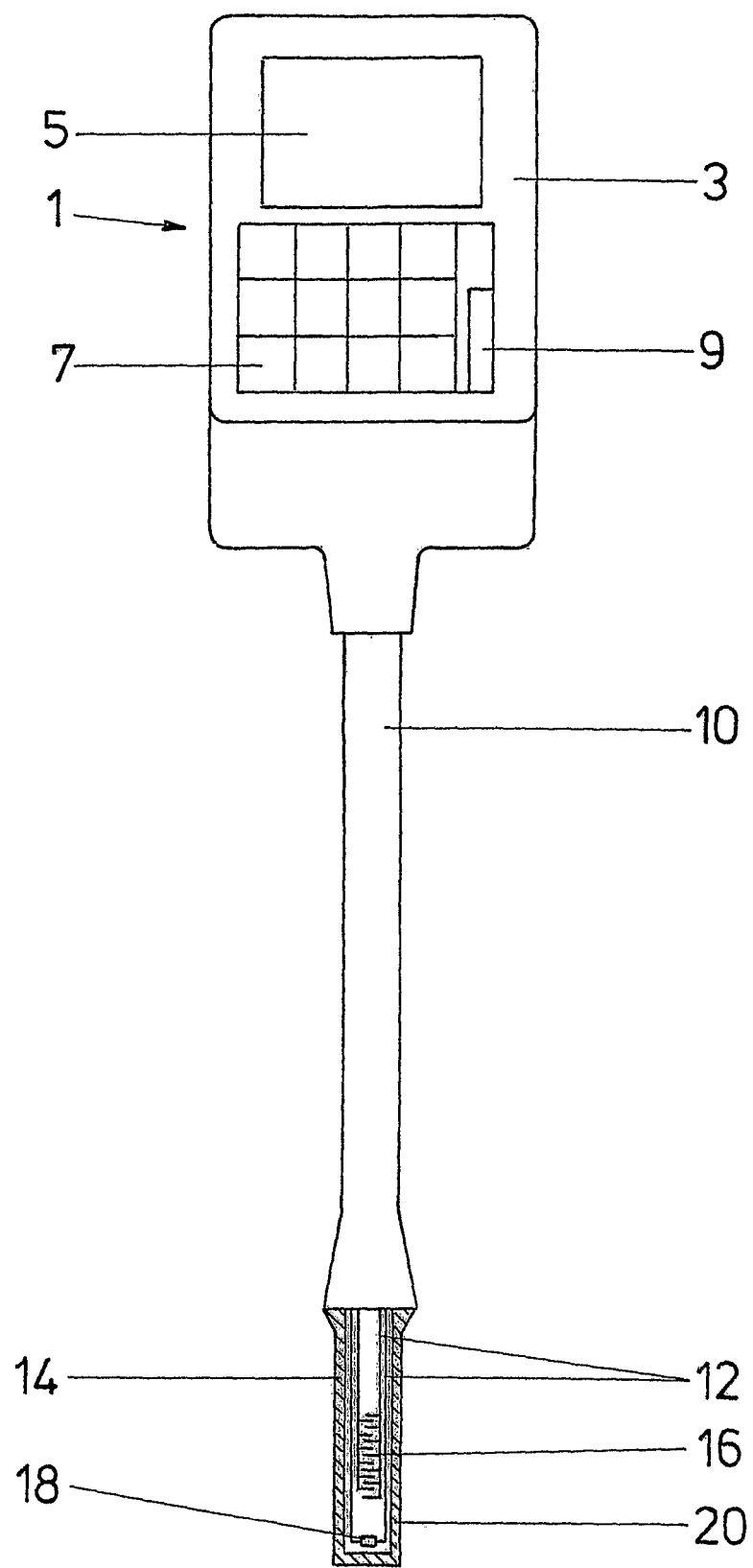
FIG. 1 shows a measuring device according to an embodiment of the present invention in front view.

FIG. 1 shows a measuring device 1 according to the present invention for measuring the state of oils or fats, which has a housing 3 in its upper area. The housing has a display 5 for displaying measured values. The display is preferably designed as an LCD display and is switchable between graphic display, e.g., color coding of the measured values, and numerical display. A keyboard 7 is provided for inputting control instructions, via which instructions may be issued to the central control unit (not shown). Keyboard 7 is preferably designed as a membrane keyboard. The housing may preferably also have an interface 9, which may be used for communication with external computers. Measuring device 1 is preferably designed to perform self-calibration. During the use of measuring device 1, housing 3 is simultaneously used as a handle for the operator.

A hollow connecting element 10, which is sufficiently long and is made of a poorly heat-conducting material, protrudes downward from housing 3, so that the sensitive electronic analyzer circuit (not shown) of measuring device 1, which is located in the area of housing 3 and/or in the area of connecting element 10 facing housing 3, is adequately protected against the heat of the oil or fat to be measured. These measures ensure that the operator is able to safety perform the measurements. Connecting element 10 is preferably made of stainless steel, which, in addition to its low thermal conductivity, is also suitable because of its unrestricted applicability in the food industry. Connecting element 10 is preferably designed as a tubular component and is suitable for receiving electric conductors 12 running inside connecting element 10. Electric conductors 12 are situated on flat substrates 14, 15, arranged in series, which are characterized by their electrical insulating properties, for example, on substrates 14, 15 made of a ceramic material.

In the lower area of first substrate 14, there is a sensor 16 for measuring electrical properties of the oil or fat and, preferably, a temperature sensor 18, whose measured values are conducted via electric conductors 12 on substrates 14, 15 to the electronic analyzer circuit. A protective means 20 for protecting sensors 16, 18 against external influences, in particular against contact with the bottom or the walls of the measuring container, may be applied around the lower area of substrate 14. In the present case, protective means 20 is designed as a peripheral edge of flat first substrate 14, connected to connecting element 10.

The gap between first substrate 14 and connecting element 10 is insulatingly sealed at one point via suitable sealants 22 (not shown). In the lower end area of connecting element 10, a suitable adhesive, for example, a silicone adhesive, is injected into the gap between first substrate 14 and connecting element 10, so that these are not in direct contact and thus are insulated from one another. At the same time, the adhesive functions as a seal of connecting element 10, so that no oil or fat is able to penetrate into the inside of connecting element 10. The adhesive surface must reliably prevent water inclusions; otherwise an explosion risk, as well as contamination of the oil or fat to be measured may result.

Figure 2:
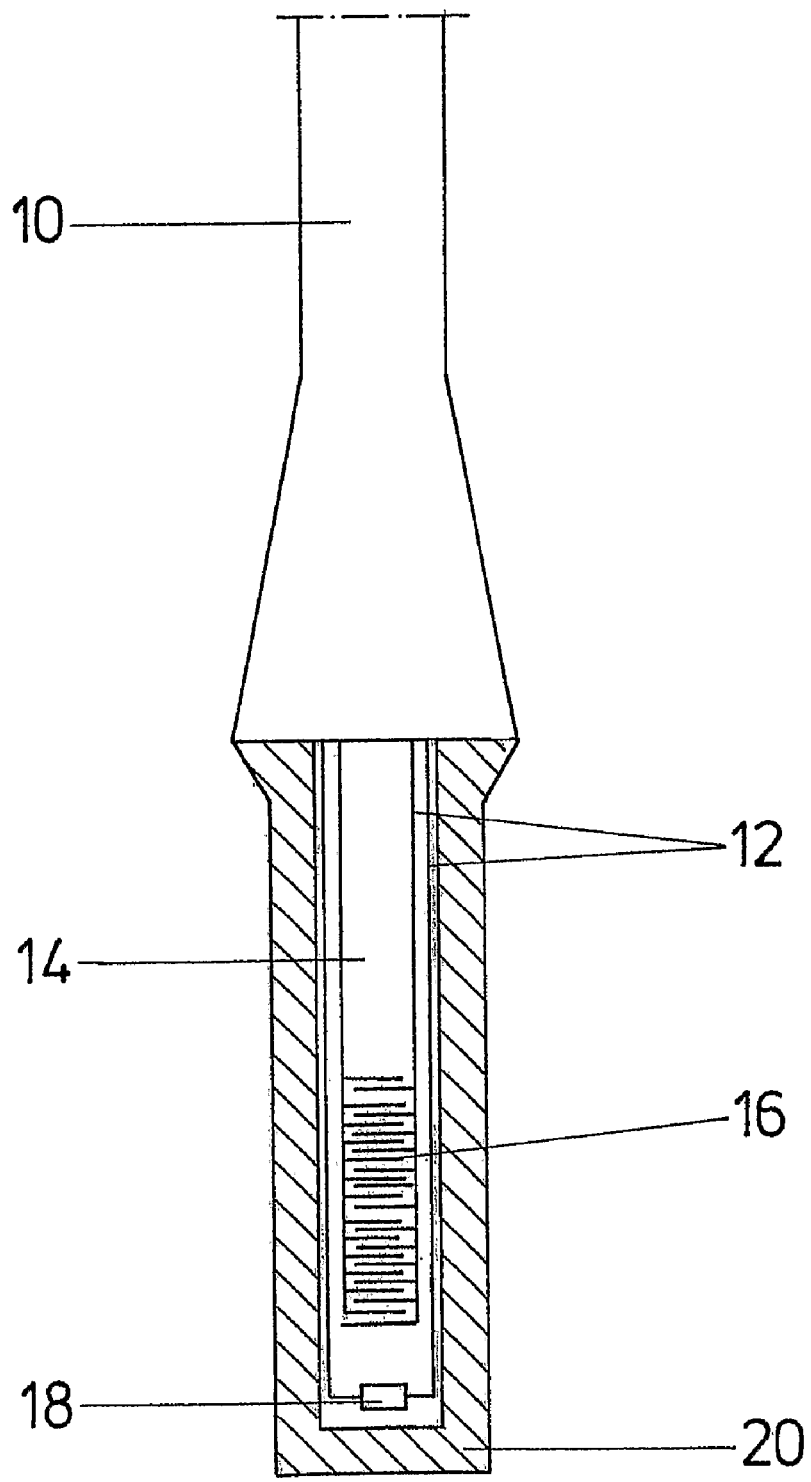
FIG. 2 shows an enlarged view of the lower area, to be immersed, of the measuring device of FIG. 1.

FIG. 2 shows an enlarged view of the lower sections of connecting element 10 and of first substrate 14, which are suitable for being immersed into the liquid to be measured. Sensor 16 for measuring the dielectric constant has a capacitor which measures the dielectric constant of the oil. It is preferably designed as an interdigital capacitor which has fine intermeshing metal conductors each of which continues as electric conductor 12 leading to the electronic analyzer circuit. Conductors 12 may be made of a fine plating of gold or copper for example on the particular substrate 14, 15, the plating being printed directly onto the ceramic component.

Temperature sensor 18 is designed, for example, as an electrical resistor, which may be made of platinum for example or another suitable material. Temperature sensor 18 may also be situated on the opposite side of substrate 14 in the area of the tip of substrate 14, which makes it possible to further reduce the size of the measuring device, while exposing both sensors 16, 18 to the same ambient temperature.

Figure 3:
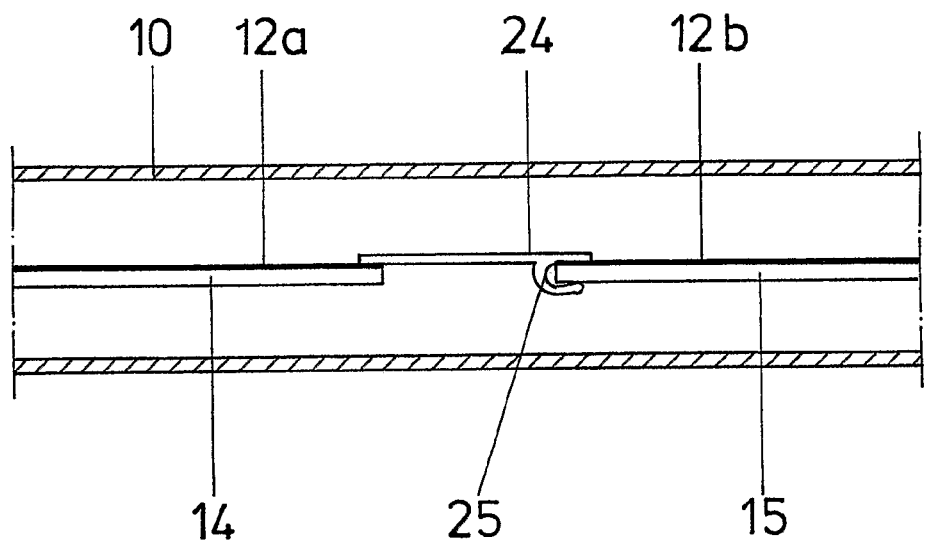
FIG. 3 shows a longitudinal section through a transition area between two substrates of the measuring device according to an embodiment of the present invention.

FIG. 3 shows a longitudinal section through a specific embodiment according to the present invention of the multipart substrate system within connecting element 10. Conductors 12, situated on first substrate 14 and connected to sensors 16, 18, are connected, in the transition area, to connectors 12b situated on substrate 15 and leading to the electronic analyzer circuit, via suitable metallic connecting elements 24, while substrates 14 and 15 are not in direct contact. In the present case, connecting element 24 is designed as a connecting clip which is attached, for example soldered, to first substrate 14, surrounding and securing second substrate 15 with the aid of a U-shaped end section 25. A mechanically stable electrical connection is thus established between substrates 14 and 15. Each conductor 12 has its own connecting clip. However, other known connecting mechanisms may also be used: simple soldering of connecting bridges 24 to the two substrates 14, 15; connecting clips having a U-shaped end segment 25 on either side; connecting plugs and sockets; connections via flat cables, etc. More than two substrates may also be arranged in series. By thermally isolating the individual substrates, heat can only be transferred via electric conductors 12, which substantially reduces the risk of overheating of the electronic analyzer circuit. Further reduction of the heat injected into substrate 14 is achieved if conductors 12a on substrate 14 have small cross-sections, since the preferred material, copper, has high thermal conductivity. It is advantageous if the continuation of conductors 12b on substrate 15 are designed as flat track conductors, so that maximally homogeneous temperature distribution is obtained over the width of the substrate.

Figure 4:
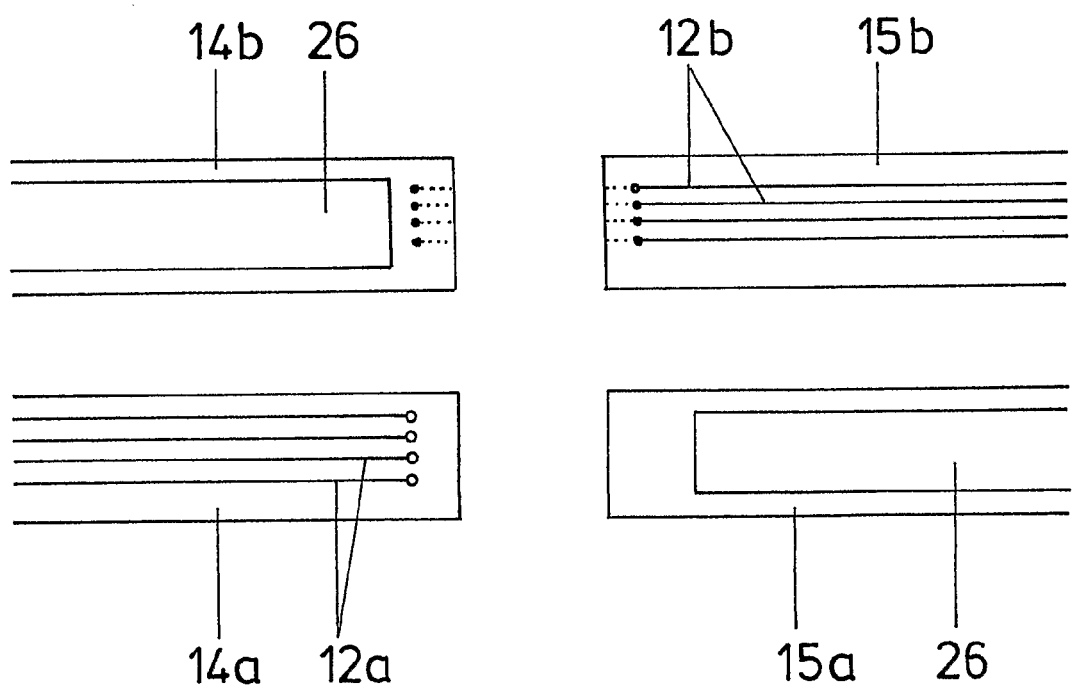
FIG. 4 shows a view from below of two substrate layers.

Another option for homogeneous heat distribution is provided by using substrates having a plurality of layers. FIG. 4 shows the individual substrate layers of a dual-layer substrate system viewed from below, the lower layer of first substrate 14 being labeled with the numeral 14a, the upper layer of first substrate 14 with 14b, the lower layer of second substrate 15 with 15a, and the upper layer of second substrate 15 with 15b. When assembled, the bottoms of substrate layers 14b and 15b are applied to the tops of substrate layers 14a and 15a, respectively.

Conductors 12a on first substrate 14 run initially on the bottom of substrate layer 14a and then, through substrate layers 14a and 14b, exit at the top of substrate layer 14a. From there, a connection (not shown) is established, in the previously described manner, to electrical conductors 12b on the top of substrate layer 15b, which then continue to the bottom of substrate layer 15b. In order to reinforce the uniform heat distribution, in areas having no conductors 12 and no direct contact with the oil or fat to be measured, compound areas 26 is applied to portions of the surface, in the present exemplary case, to the bottom of substrate layers 14b and 15a. The specific heat of the compound areas also prevents a more rapid increase in the temperature of substrate 14, 15.

In addition to the specific embodiments shown, many other exemplary embodiments of the present invention are conceivable in which similar geometric arrangements of the individual components are used. It is possible, in the first place, to use substrates 14, 15 having more than two layers and to vary the course of conductors 12 and the arrangement of compound areas 26 in almost any conceivable way.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A measuring device for measuring the state of oils or fats, comprising:
 a housing;
 a hollow connecting element attached to the housing, wherein at least one electrical conductor runs inside the hollow connecting element;
 a plurality of substrates mounted on the opposite end of the connecting element for receiving a sensor for measuring an electrical property of oil or fat to be measured, the connecting element being thermally insulated from the plurality of substrates, the sensor being connected to an electronic analyzer circuit via the at least one electrical conductor situated on at least one of the plurality of substrates that is a non-conductive substrate, the electronic analyzer circuit being situated in the area of at least one of: the housing and the end of the connecting element facing the housing, wherein the plurality of substrates includes a plurality of electrically connected and thermally isolated carrier substrates arranged in series, each of the plurality of electrically connected and thermally isolated carrier substrates having electrical conductors situated thereon.

2. The measuring device as recited in claim 1, wherein electrically conductive connecting elements are situated at connecting points of the substrates.

3. The measuring device as recited in claim 1, wherein the electrical conductors have a small cross-section in the area of the sensor on a first substrate.

4. The measuring device as recited in claim 1, wherein the electrical conductors have a large cross-section toward the electronic analyzer circuit.

5. The measuring device as recited in claim 1, wherein at least one substrate has a plurality of layers.

6. The measuring device as recited in claim 1, wherein the substrates are situated at a distance from one another.

7. The measuring device as recited in claim 6, wherein a thermally insulating material is provided between the substrates.

8. The measuring device as recited in claim 7, wherein air is provided as the thermally insulating material.

9. The measuring device as recited in claim 1, wherein the individual substrates are made of different materials, so that the electrical and mechanical properties of the substrates can be optimally adjusted to the components.

10. The measuring device as recited in claim 9, wherein the different materials include ceramic, plastic, metal and composite materials.

11. The measuring device as recited in claim 1,
wherein the electrical conductors have a small cross-section in the area of the sensor on one of the substrates and a large cross-section toward the electronic analyzer circuit,
wherein at least one substrate has a plurality of layers, and
wherein a thermally insulating material is provided between each of the plurality of substrates.

12. A measuring device for measuring the state of oils or fats, comprising:
a housing;
a hollow connecting element attached to the housing;
a plurality of substrates mounted on the opposite end of the connecting element for receiving a sensor for measuring an electrical property of oil or fat to be measured, the sensor being connected to an electronic analyzer circuit via at least one electric conductor situated on at least one of the plurality of substrates that is a non-conductive substrate, the electronic analyzer circuit being situated in the area of at least one of: the housing and the end of the connecting element facing the housing, wherein the plurality of substrates includes a plurality of electrically connected and thermally isolated substrates arranged in series, and electrical conductors situated thereon, wherein at least one substrate has a plurality of layers, and wherein at least one layer of the substrate has a compound area in regions that have no conductors and no contact with the oil or fat to be measured.

13. A measuring device for measuring the state of oils or fats, comprising:
a housing;
a connecting element having a first end coupled to the housing, wherein at least one electrical conductor runs inside the connecting element;
a plurality of substrates disposed at a second end of the connecting element, the substrates being electrically connected carrier substrates and substantially thermally isolated from each other, the connecting element being thermally insulated from the plurality of substrates;
a plurality of electrical conductors disposed on the plurality of electrically connected and substantially thermally isolated carrier substrates;
an analyzer circuit disposed in an area of at least one of the housing and an end of the connecting element facing the housing; and
a sensor for measuring a property of oil or fat to be measured, the sensor being disposed on at least one of the plurality of substrates and coupled to the analyzer circuit.

14. The measuring device as recited in claim 13, wherein electrically conductive connecting elements are situated at connecting points of the plurality of substrates.

15. The measuring device as recited in claim 13, wherein the electrical conductors have a smaller cross-section in the area of the sensor on a first substrate and a larger cross-section toward the analyzer circuit.

16. The measuring device as recited in claim 13, wherein at least one substrate has a plurality of layers.

17. The measuring device as recited in claim 13, wherein a thermally insulating material is provided between the substrates.

18. The measuring device as recited in claim 13, wherein at least two substrates of the plurality of substrates are made of different materials.

19. The measuring device as recited in claim 18, wherein the different materials include at least one of ceramic, plastic, metal and composite materials.

20. A measuring device measuring the state of oils or fats, comprising:
a housing;
a connecting element having a first end coupled to the housing;
a plurality of substrates disposed at a second end of the connecting element, the substrates being electrically connected substrates and substantially thermally isolated from each other;
a plurality of electrical conductors disposed on the plurality of substrates;
an analyzer circuit disposed in an area of at least one of the housing and an end of the connecting element facing the housing; and
a sensor for measuring a property of oil or fat to be measured, the sensor being disposed on at least one of the plurality of substrates and coupled to the analyzer circuit, wherein at least one substrate has a plurality of layers, and wherein at least one layer of the substrate has a compound area in regions that have no conductors and no contact with the oil or fat to be measured.

* * * * *